(12) United States Patent
Tanaka (10) Patent No.: US 8,696,954 B2
(45) Date of Patent: Apr. 15, 2014

(54) METHOD, SYSTEM, AND COMPOSITION FOR COLORING CERAMICS

(75) Inventor: Asami Tanaka, Skokie, IL (US)

(73) Assignee: Tanaka Dental Products, Skokie, IL (US)

( * ) Notice: Subject to any disclaimer, the term of this patent is extended or adjusted under 35 U.S.C. 154(b) by 447 days.

(21) Appl. No.: 12/950,997

(22) Filed: Nov. 19, 2010

(65) Prior Publication Data

US 2011/0306017 A1 Dec. 15, 2011

Related U.S. Application Data

(60) Provisional application No. 61/353,035, filed on Jun. 9, 2010.

(51) Int. Cl.
*A61C 13/00* (2006.01)

(52) U.S. Cl.
USPC .......................................................... 264/20

(58) Field of Classification Search
USPC .......................................................... 264/20
See application file for complete search history.

(56) References Cited

U.S. PATENT DOCUMENTS

| | | | | |
|---|---|---|---|---|
| 2,682,480 A | * | 6/1954 | Andrews | 427/282 |
| 4,264,307 A | | 4/1981 | Neuwirth | |
| 4,481,227 A | * | 11/1984 | Tanaka | 427/2.29 |
| 5,618,585 A | | 4/1997 | Hechler et al. | |
| 5,869,548 A | | 2/1999 | Ikushima et al. | |
| 6,709,694 B1 | | 3/2004 | Sutter et al. | |
| 8,178,012 B1 | * | 5/2012 | Khan et al. | 264/20 |
| 2002/0110787 A1 | * | 8/2002 | Abiru et al. | 433/224 |
| 2003/0158111 A1 | | 8/2003 | Bar-Or | |
| 2003/0207235 A1 | | 11/2003 | Der Zel | |
| 2005/0123880 A1 | | 6/2005 | Grundler et al. | |
| 2009/0047633 A1 | * | 2/2009 | Huo et al. | 433/217.1 |
| 2012/0214134 A1 | | 8/2012 | Khan et al. | |

OTHER PUBLICATIONS

Brewer et al, Advances in Color Matching, Dent Clin N Am, 2004, 341-358, 48, USA.

Ishikawa-Nagai, Clinical Evaluation of perceptibility of color differences between natural teeth and all ceramic crowns, J Dent, 2009, USA.

* cited by examiner

*Primary Examiner* — Joseph S Del Sole
*Assistant Examiner* — Erin Snelting
(74) *Attorney, Agent, or Firm* — Schafer Smith LLC (57) ABSTRACT

A system, method and composition for coloring dental ceramics. The system, method, and composition resulting in natural color matching without drying time between color layers. The system, method and composition also resulting in good color preparation on restorations of about 0.001 mm-1.000 mm thickness.

3 Claims, 5 Drawing Sheets

METHOD, SYSTEM, AND COMPOSITION FOR COLORING CERAMICS

RELATED APPLICATIONS

The present patent document claims the benefit of the filing date under 35 U.S.C. §119(e) of Provisional U.S. Patent Application Ser. No. 61/353,035 filed Jun. 9, 2010, which is hereby incorporated by reference.

BACKGROUND

Often during sporting, automobile accidents, or due to illness or disease, individuals may lose one or more teeth. The loss of teeth may result in loss of integrity of the bite. Also, many individuals are uncomfortable with the appearance of missing teeth. The dental arts have established technology to create artificial teeth that mimic an individual's original teeth. For example, the dental arts, using ceramics, can mold teeth that look mimic natural teeth.

Among others, zirconia is a popular material from which dental replacements are made. However, zirconia creates a very hard surface which is not easily colored. Zirconia also requires firing at temperatures over 900° C. At that temperature, the pigments traditionally used to color dental ceramics disappear and lose color. Presently it is the knowledge of that art that no stains or other colorants will adhere or bond to Zirconium ceramics.

Zirconia is a very strong material and the dental sciences are quickly adopting zirconia ceramics for use in dental restorations. However, a drawback to the use of zirconia is the stark white color of the material. Most individuals prefer dental restorations which have the appearance and color of a natural tooth. Specifically, individuals wish to have dental restorations that blend in naturally with the remaining teeth.

BRIEF SUMMARY

A system, method and composition for coloring dental ceramics. The system, method, and composition resulting in natural color matching without drying time between color layers. The system, method and composition also resulting in good color preparation on restorations of about 0.001 mm-1.000 mm thickness.

DETAILED DESCRIPTION

Dental restoration after tooth loss is quite popular to improve the visible appearance of the face and also to restore the integrity of the bite. Individuals who have suffered tooth loss may want their restorations to have a natural appearance and match in size, shape, and color, their natural teeth. Aesthetically pleasing replacements are increasingly sought after.

Technologies, such as CAD/CAM technology may be used in dentistry to help dentists and dental technicians fabricate precise shapes and sizes for dental restorations, including, for example, inlays, onlays, crowns, and bridges. Dentists may use CAD/CAM and other related technologies to provide their patients with durable, well-fitted single and multiple tooth restorations.

Dentists and dental technicians may use CAD/CAM and other technologies to design the anatomical features, size, and shape of a tooth restoration, for example but not limited to, on a computer. For example, with CAD/CAM, the machine fabricates the restoration through a milling chamber that crafts the tooth-like ceramic material into a precise replica of the drawing.

There are many different materials used for making dental restorations. Among them, ceramic may be used for in-lays, on-lays, crowns, veneers, as well as full restorations, among others. For example, full ceramic restorations are particularly desirable because their color and translucency mimic natural tooth enamel.

Computerized dentistry, such as by the use of CAD/Cam technology, has enabled the application of zirconium-oxide ($ZrO_2$). The introduction of this zirconium in restorative and prosthetic dentistry may have encouraged the use of full ceramics without limitation. With the exception of zirconium-oxide, existing ceramics systems may lack reliable potential for the various indications for bridges without size limitations. Zirconium-oxide with its high strength and comparatively higher fracture toughness may be more reliable than existing ceramic systems. With a three-point bending strength exceeding 900 megapascals, zirconium-oxide may be used in virtually every full ceramic prosthetic solution, including bridges, implant supra structures and root dowel pins.

As technology improves, more stringent requirements are being placed on the aesthetics of teeth. Metals and porcelain may currently be the materials of choice for crowns and bridges. The demand for full ceramic solutions, however, continues to grow. Consequently, industry and science are increasingly compelled to develop full ceramic systems. In introducing full ceramic restorations, such as base structures made of sintered ceramics, more attention must be focused on developing a coloring system that improves the natural appearance of the ceramics.

The super hard surface that makes zirconia appealing for ceramic restorations, does not lend itself to easy coloration. Disclosed herein is a method, system, and composition that may be used to impart a natural color to dental restorations. The method, system, and device may eliminate the need to use mask layers of opaque and body porcelains. The method, system, and solution may be capable of preparation on the edge of a knife and may eliminate the need to shoulder prep for color.

Additionally, the method, system, and composition may require short or no drying time and multiple applications of different shades may be possible. Application of the method, system, and composition may result in a three dimensional appearance of the dental restoration.

Two systems are disclosed. A first system relates to pre-sintering coloring of dental ceramics. A second system relates to post-sintering coloring of dental ceramics. Also disclosed is a method of minimally invasive dental restoration.

Pre-Sintering Coloring of Dental Ceramics

Dental restorations are commonly prepared with a substructure of a metal or ceramic material upon which substructure layers of porcelain are applied. For example, ceramic or metal alloy substructures may be first covered by an opaque layer, followed by an opacious dentin layer, a dentin layer and finally an incisal porcelain layer.

Aesthetics of the dental restoration is of great importance. Patients desire a natural appearance of the prosthesis. In order to achieve a natural appearance of the prosthesis, the dental technician must carefully match and color the framework or facing ceramics. A natural appearance relies not only on color, but on translucence. Currently, most coloring systems require several procedures and layers which are finally fired (sintered) in an oven. The current coloring systems are therefore time consuming and expensive. Additionally, the current coloring systems may not provide a satisfactory level of natural appearance. For example, dental implants created under current coloring systems often have a shadow from the cast metal. Increased numbers of ceramic layers may be used to mask the shadow from the cast metal, however, to accommodate the increased number of layers, the dental professional must remove an equivalent amount of tooth material. The removal of tooth material, for example, removal of enamel that compromises the integrity of the dentine layer, has lead to the observation that over 22% of restored teeth decay after 5 years.

We disclose herein a dental restoration color system that allows for a natural tooth color result with less preparation time, increased color stability upon firing, and requiring less material therefore less invasive tooth preparation.

The disclosed system is particularly applicable to zirconium restorations. Zirconium restorations provide increased strength and better fit while also having excellent biological compatibility, which may prevent or reduce gum erosion.

Figure 1:
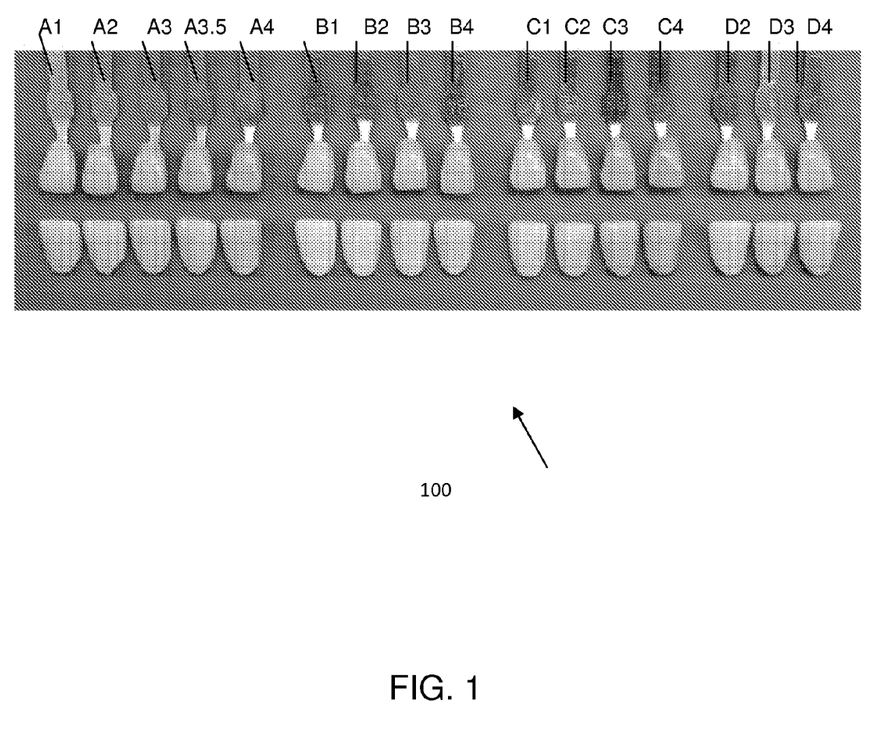
FIG. 1 illustrates the range of natural colors achieved with the disclosed system, method, and composition.

A coloring system for dental ceramics may include may include, among other items, a series of color liquids. The color liquids may be formulated in a wide range of incisal and gingival shades for color matching natural dentition, see FIG. 1, 100 for a visual example of one variation of color shades disclosed herein. The series of color liquids may be given reference numerals for identification of the color of the natural dentition. An example of a series of reference numerals may be: A1, A2, A3, A3.5, A4, B1, B2, B3, B4, C1, C2, C3, C4, D2, D3, D4, Incisal Light, Incisal Dark, Occlusal, and Pink. See FIG. 1.

The liquid compositions of the system may be formulated to dry quickly and may not require preheating prior to sintering. The liquid compositions of the system may be applied by dipping or may be applied by brushing, or any other way. Application of the liquid composition by brushing may allow for the application of different shades both inside and outside of the restoration.

Dental restoration materials may be provided in blocks of material, for example, dental zirconia ceramic blocks. Dental equipment, such as the CAD/Cam technology, may be used to mill the solid blocks of the restoration material, such as zirconia ceramic, into a dental restoration such as but not limited to a bridge, tooth, cap, or other structure.

In one example of preparation of dental restorations, a block of material, for example, a dental zirconia ceramic block or disk, may be prepared by, for example, cold isostatic pressing of zirconia powders.

CAD/CAM restorations may be milled from solid blocks of white composite resin or may be made from porcelain matching the shade of the restored tooth. An exemplary process involves taking an image of the defective tooth area. This image may be used to draw the data into a computer and proprietary software may be used to create a a virtual restoration. The software may then send this virtual data to a milling chamber by the dentist where the dental restoration is carved out of a solid block of, for example, composite resin or porcelain. The resultant restoration can then be adjusted in the patient's mouth and bonded in place.

If porcelain is used, practitioners may treat the restoration with stains and glazes and subsequent heat treatments to both beautify and strengthen the definitive restoration prior to bonding. Practitioners may perform acid etching of both the underside of the restoration and the topside of the tooth itself, which may microscopically increases surface area on both opposing surfaces. Practitioners may then use composite resin materials to fuse the resultant restoration to the tooth, completing the restoration process.

Currently, using available methods, staining and glazing to match the patient's natural tooth color is a complicated and time consuming process. For example, in order to achieve a natural appearance of the restoration, the tooth color and the translucence must be simulated over several layers. For example, practitioners may use intermediate layers such as dye pastes or dye suspensions, which may require several applications, each application requiring and individual setting and drying time. After several procedures, the restoration may be fired in an oven. This process is time- and cost-intensive.

In another method, described in U.S. Pat. No. 6,709,694, color reagents are dissolved in water. Ceramic restorations are then steeped in the reagent for 5 minutes and then dried and sintered. Finally, after the steeping and drying times, the restoration may be dried and sintered.

In another method and system, provided by VITA, a restoration is dipped into the coloring liquid and dried. Each application requires a color reaction time and a color drying time. The method also includes steps of prebaking and preheating and requires the use of hydrochloric acid. Available coloration liquids, such as but not limited to the VITA liquids are thick and they do not penetrate the ceramic.

The formulation of the disclosed system of compositions provides a unique and surprising feature of requiring no drying time between layers.

The disclosed technology may enable the dentist, dental technician, or ceramist to reproduce the subtleties of natural dentition, for example, matching a zirconia crown to a natural root. Furthermore, the technology may disguise opacity, and may enhance translucency, and may provide subtle characterization for a natural looking result.

The technology may be supplied in a kit, for example, a kit that contains one of 5, 10, 15, 20, 25, 30, or more shades. The kit may also include a shade guide which is matched to the shades of the system. The kit may also include a thinner.

The method of using the system may be as follows. However, other methods are foreseen, therefore the following is a non-limiting description of one method of using the system.
1. Prepare the Zirconia Surface Dust may be removed from the zirconia understructure. For example, dust may be completely removed from the zirconia understructure, especially the inside incisal and angle regions. A firm bristled brush, for example but not limited to a CLEANUP BRUSH may be used to remove the dust.

Mark the regions to be stained, for example, the cervical, body, and incisal. Marking may be made on the surface of the zirconia, for example, using a graphite pencil. The marks may disappear during firing.
2. Select Your Colors Choose coloring liquids suitable for the areas to be shaded. In one example, both the outer and inner surfaces of a zirconia understructure may be treated which may produce a translucent effect. In another example, when restoring discolored teeth, inner surfaces may not be stained which may help retain the original opacity of the zirconia.

Colors may be chosen by using a color guide which may be included, for example, with a kit of the system. In one example, the liquid compositions may be formulated to match the shades of, for example but not limited to, the VITA CLASSIC SHADE GUIDE.

For cervical, connector, and lingual regions of the zirconia understructure, one may choose a color one or two ranks darker than the reference shade. For example, if the reference color is A2, one may choose the shade of the system referenced by A3 or A3.5. For incisal regions, one may choose Incisal Light or Incisal Dark of the system.

3. Apply Colors

Each color liquid of the system may be shaken well before using. One may apply the color using an applicator brush. The applicator brush may be dipped into the liquid of the system and any excess color may be removed against the edge of the bottle.

The color liquid of the system may be applied quickly to unsintered zirconia. Unsintered zirconia is porous and may absorb more colorant than required if the applicator brush is held against its surface for too long. One may elect to treat the incisal portion of the understructure before the body portion. This may prevent surfacing of the darker body color.

The dipping and painting with the disclosed liquid may be effective after a 1 second application and subsequent layers may be applied with no drying time in between. The disclosed colorant may penetrate through a 3 mm or larger sample with no preheating required. The disclosed colorant may be used at room temperature or may be used at 300° C. or any other temperature. After application of the disclosed colorant, the restoration, such as a Zirconia restoration, may be sintered in an oven that naturally increases from approximately 300° C. to approximately 1380° C. over a period of 7-8 hours.

One may use the STAIN BRUSH or the TOUCHUP BRUSH and may apply three coats of the chosen liquid composition, for example, Incisal Light or Incisal Dark liquid, to the margins and occlusal surfaces. Applying the liquid in vertical strokes may prevent the appearance of horizontal stripes.

The reference body color may be applied to the remaining surfaces two or three times. Additional applications may be desired, for example, if the zirconia understructure is relatively thick.

4. Sinter

The system may not require prefiring. The normal sintering process may proceed as soon as the zirconia surface is dry to the touch.

Process

Each ingredient must be measured very accurately by weight and not by volume. For the solutions that are made with a very low percentage of raw materials, the raw materials may be diluted with D-Limonene 100 times and then measured before mixing with other ingredients. This stage should be performed without the application of heat.

Quality Control

After each color solution has been mixed, one may take a thin, pre-sintered, sample of zirconia, for example an approximately 0.5 mm×10 mm×20 mm in size sample, and may dip/soak it in the solution for up to 10 seconds.

After applying the sample color, quickly remove and excess color solution from the zirconia sample, for example, using an air gun or a piece of tissue paper.

Take the liquid color treated zirconia sample to the sintering over and heat it at normal temperature for zirconia sintering program process. The heat should be for example but not limited to 1500+/− Celsius. After sintering, allow the treated zirconia chip to cool to room temperature. Examine the color of the sintered zirconia.

Each batch of colorant solution may be checked to insure color quality and uniformity. Slight variations of color may occur between different batches that are mixed, and/or if the raw materials are acquired from different suppliers or vendors.

Technical Specifications

For the solutions that are made with a very low percentage of raw materials, the raw material may be diluted with D-Limonene 100 times then measured before mixing with other ingredients.

The Coloration process formulary may include the following: Chromium 2-Ethylhexanoate, Iron 2-Ethylhexanoate, Cobalt 2-Ethylhexanoate, Manganese 2-Ethylhexanoate, Copper 2-Ethylhexanoate, Zirconium Carboxylate, Yttrium Carboxylate, Zinc 2-Ethylhexanoate, D-Limonene: formula: C10H16 (natural) CAS#5989-27-5 TSCA; Soya Ester (Natural), Mineral Spirit (Petroleum HYdroCarbon).

For example, Coloring Material Ingredients may include: 6% Iron Hex-Cem® Solution (iron octoate), 8% Chromium Hex-Cem® (chromium octoate), 24% Zirconium Hex-Cem® (zirconium octoate), 6% Manganese Hex-Cem® (manganese octoate), 8% Nickel Hex-Cem® (nickel octoate), and/or 6% Cobalt Hex-Cem® (cobalt octoate). Ingredients may also include CK D-Limonene Hydrocarbon.

The following formulary chart provides an exemplary system of coloration liquids. These are for illustrative purposes only and are not limiting.

|  | A1 | A2 | A3 | A3.5 | A4 |
| --- | --- | --- | --- | --- | --- |
| Fe | 4.0-6.0% | 8.5-10.5% | 11-15% | 16-20% | 20%-23% |
| Cr | 0.01-1.0% | 0.01-1.0% | 0.01-1.20% | 0.01-1.5% | 0.01-1.3 |
| Zr | 3.0-5.0% | 4.5-7.0% | 4.5-6.5% | 3.0-7.0% | 4.0-6.5% |
| Mn | 0.0-1.5% | 0.0-1.5% | 0.0-1.5% | 0.0-1.5% | 0.001-1.0% |
| Ni | 0.0-1.5% | 0.0-1.5% | 0.0-1.5% | 0.0-1.5% | 0.0-1.5% |
| D-Limonene | balance | balance | balance | balance | balance |

|  | B1 | B2 | B3 | B4 | Occlusal |
| --- | --- | --- | --- | --- | --- |
| Fe | 4.0-7.0% | 6.5-10.5% | 10-15% | 16-22% | 35-45% |
| Cr | 0.0-1.5% | 0.0-1.5% | 0-0.5% | 0.0-1.5% | 0.01-1.3 |
| Zr | 3.0-5.0% | 4.5-7.0% | 4.5-6.5% | 0.0-1.5% | 4.0-7.5% |
| Mn | 0.0001-1.0% | 0.001-1.0% | 0.0001-0.5% | 0.0-1.0% | 0.0-1.0% |
| Ni | 0.01-1.0% | 0.01-1.2% | 0.10-2.0% | 0.0-1.5% | 0.0-1.5% |
| D-Limonene | balance | balance | balance | balance | balance |

-continued

|   | C1 | C2 | C3 | C4 | D2 |
|---|---|---|---|---|---|
| Fe | 7.5-10.5% | 14.5-18% | 15-19% | 16-22% | 4.0-6.5% |
| Cr | 0.0-1.5% | 0.0-1.5% | 0-0.5% | 0.0-1.5% | 0.0001-1.0% |
| Zr | 3.0-6.0% | 4.0-7.0% | 4.0-6.5% | 4.0-7.0% | 3.0-6.0% |
| Mn | 0.0001-1.0% | 0.0-1.0% | 0.0-1.0% | 0.01-1.2% | 0.0-1.2% |
| Ni | 0.00-1.0% | 0.0-1.2% | 0.0-1.2% | 0.0-1.2% | 0.0-1.2% |
| Co | 0.00-1.0% | 0.0-1.2% | 0.0-1.2% | 0.0-1.2% | 0.0-1.2% |
| D-Limonene | balance | balance | balance | balance | balance |

|   | D3 | D4 | Inc Dark | Inc Light | Pink |
|---|---|---|---|---|---|
| Fe | 7.5-10.5% | 8.5-12% | 0-1.2% | 0-1.2% | 0.0-1.2% |
| Cr | 0.01-1.5% | 0.0-1.5% | 0-1.2% | 0-1.2% | 0.0-1.2% |
| Zr | 3.0-6.0% | 4.0-7.0% | 1.0-4.5% | 2.0-6.0% | 0.0-1.2% |
| Mn | 0.0001-1.0% | 0.0-1.0% | 0-1.0% | 0.01-1.2% | 0.0-1.2% |
| Ni | 0.00-1.0% | 0.0-1.2% | 0.01-3.2% | 0.01-2.2% | 0.0-1.2% |
| Co | 0.00-1.0% | 0.0-1.2% | 0.0-1.2% | 0.0-1.2% | 1.0-4.5 |
| D-Limonene | balance | balance | balance | balance | balance |

Each ingredient must be measured by weight, not by volume.

The following formulary chart provides a second exemplary system of coloration liquids. These are for illustrative purposes only and are not limiting.

|   | A1 | A2 | A3 | A3.5 | A4 |
|---|---|---|---|---|---|
| Fe | 5.0-6.0% | 9.0-10.5% | 13-14.2% | 18-19% | 20.5-21.9% |
| Cr | 0.001-0.70% | 0.01-0.80% | 0.01-0.90% | 0.01-.90% | 0.10-1.3% |
| Zr | 3.5-4.5% | 4.5-6.7% | 5.3-6.2% | 5.0-6.25% | 5.0-6.2% |
| Mn | — | — | — | — | 0.001-0.6% |
| Ni | — | — | — | — | — |
| D-Limonene | balance | balance | balance | balance | balance |

|   | B1 | B2 | B3 | B4 | Occlusal |
|---|---|---|---|---|---|
| Fe | 5.0-6.0% | 8.0-9.2% | 11-12.4% | 18.5-20% | 35-45% |
| Cr | — | — | — | — | 0.01-1.3 |
| Zr | 3.5-4.5% | 5.3-6.3% | 5.1-6.1% | — | 5.5-6.5% |
| Mn | 0.0001-0.5% | 0.00001-0.010% | 0-0.10% | 0.0001-0.10% | — |
| Ni | 0.10-1.0% | 0.1-1.1% | 0.10-1.25% | 0.10-1.25% | — |
| D-Limonene | balance | balance | balance | balance | balance |

|   | C1 | C2 | C3 | C4 | D2 |
|---|---|---|---|---|---|
| Fe | 8.5-9.5% | 15.5-16.5% | 16.5-17.5% | 20.5-21.5% | 5.1-6.2% |
| Cr | — | — | — | — | 0.01-1.0% |
| Zr | 4.5-5.5% | 4.5-5.5% | 4.5-5.5% | 4.5-5.5% | 3.5-4.9% |
| Mn | 0.0001-0.6% | 0.01-0.75% | 0.10-0.8% | 0.01-1.9% | — |
| Ni | — | — | — | — | — |
| Co | — | — | — | — | — |
| D-Limonene | balance | balance | balance | balance | balance |

|   | D3 | D4 | Inc Dark | Inc Light | Pink |
|---|---|---|---|---|---|
| Fe | 9.0-10.0% | 10-11% | — | — | — |
| Cr | 0.10-1.0% | — | — | — | — |
| Zr | 4.5-5.5% | 4.5-5.5% | 1.75-2.5% | 3.5-4.5% | — |
| Mn | 0.001-0.5% | 0.001-0.60% | 0-1.0% | 0.01-0.8% | — |
| Ni | — | 0.01-0.95% | 2.0-3.2% | 0.0-1.5% | — |
| Co | — | — | — | — | 2.0-3.0% |
| D-Limonene | balance | balance | balance | balance | balance |

Each ingredient must be measured by weight, not by volume.

The liquid composition may not use water or alcohol as a solvent. Rather, the liquid composition may use D-Limonene as a solvent.

Figure 2:
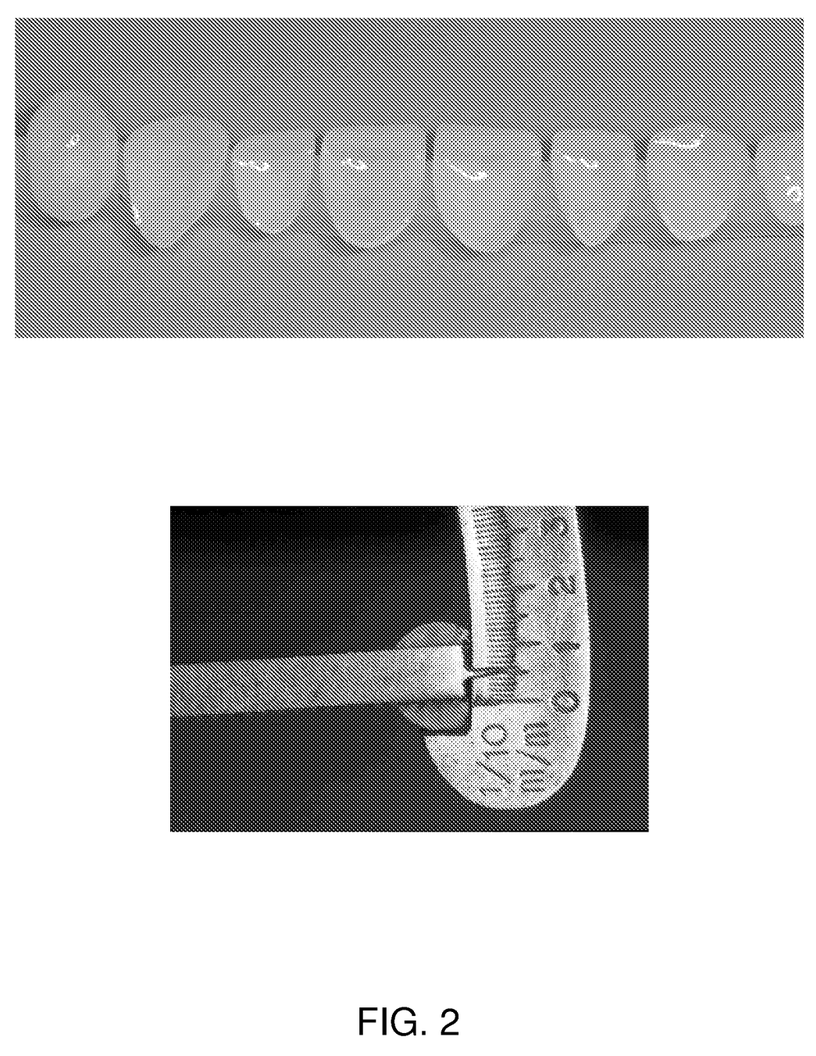
FIG. 2 illustrates the thickness of restorations.
Figure 3:
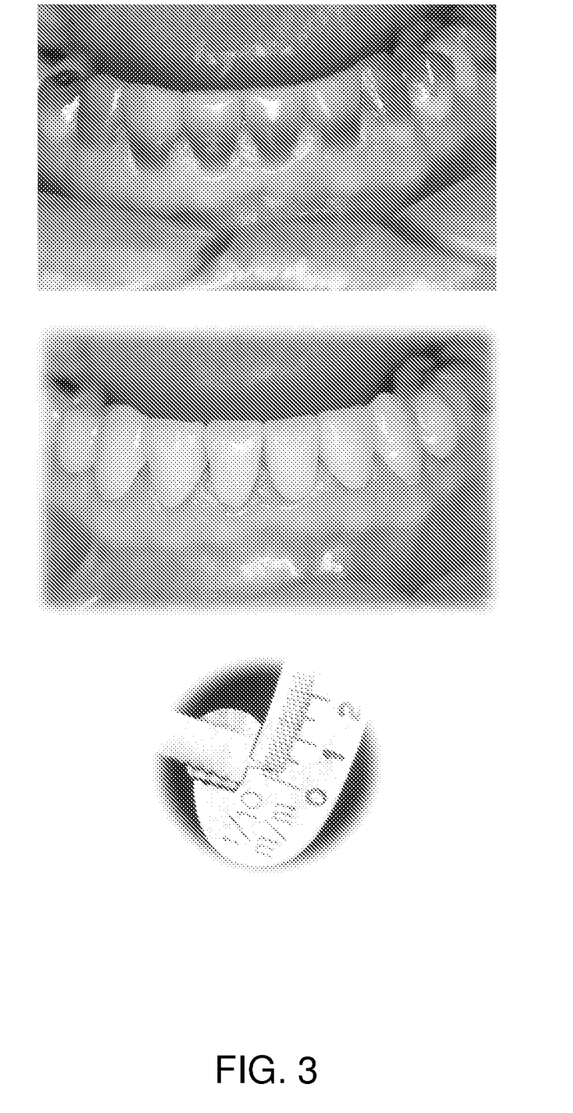
FIG. 3 illustrates the success of the thin restoration in masking underlying color defects.
Figure 4:
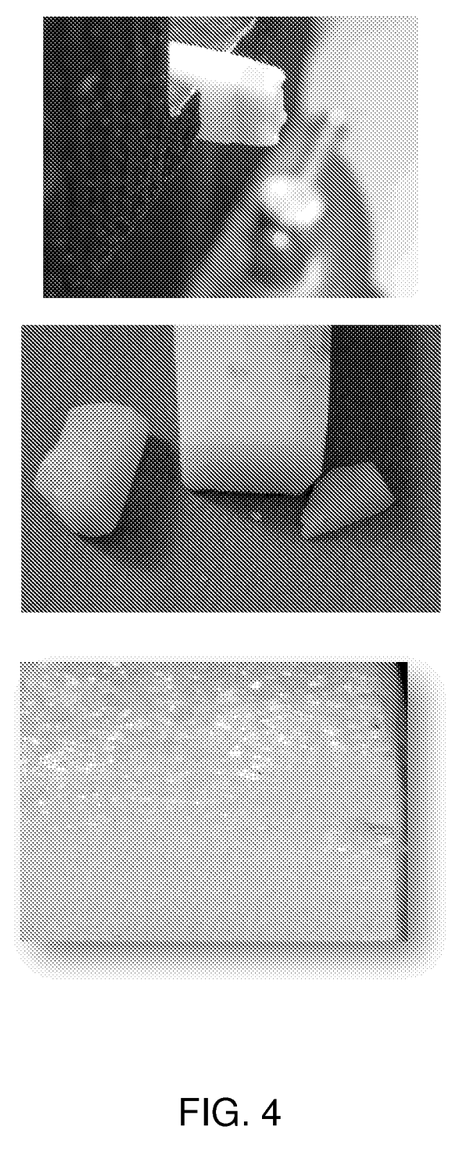
FIG. 4 illustrates the absorption of the disclosed composition.

Use of the disclosed coloring system may allow for prosthesis, crowns, and restorations that measure less than 0.5 mm in thickness as demonstrated in FIG. 2. They may further create translucence and natural color matching on a "contact lens" thickness of restoration material. FIG. 3 provides an example of the result of application of the disclosed color system. In the example of FIG. 3, the restoration showed natural color and translucence, and no shadow or show through of the underlying discoloration, even at a restoration thickness of 0.1 mm FIG. 4 demonstrates the penetration of the colorant liquid of the disclosed system.

The disclosed solutions may be used at a 6% solution or may be diluted another 10%, the solutions are applied in highly diluted form.

Commonly, it is understood that no dyes will adhere to Zirconium/yttrium ceramics due to the strength of the material. All currently marketed dye solutions rely upon applications during the pre-sintered or absorbent stage of the material. The dyes that are currently available are 02 sensitive and they are also degraded rapidly at temperatures over 900° C. Surprisingly, the disclosed compositions and systems bond to the Zirconium/yttrium restoration at temperatures over 900° C. without losing pigment. Fluorescence may be added to make the tooth look more natural. For example, fluorescence may be added with down to 0.01% glassy ceramic. Furthermore, while in the knowledge of the art, ceramic does not bond to Zirconium, it has been demonstrated that use of the disclosed liquid colorant compositions bonds the glassy ceramic layer to Zirconium.

Post Sintering Color Correction

A second system and compositions are disclosed which may be used to adjust and correct color after sintering of the restoration. Often, because of the great expense of technology such as the CAD/CAM machine, practitioners have restorations made off site. Often, although the practitioner performed careful color matching, the final restoration does not provide the appropriate natural appearance and does not blend in with the natural dentature.

It is thought in the art that post-sintering coloration of zirconium is impossible. Therefore, it was a unique and surprising result that with the disclosed system, even zirconium restorations may be color adjusted after sintering. The color powders of the post-sintering system allow for high temperature zirconia/porcelain color modification. The powders and available in a wide range of colors and allow formulation of most tooth and tissue shades straight from the bottle or in combination.

Another surprising result is that, with the post-sintering coloration system and compositions disclosed herein, there is no need to sandblast the post-sintered restoration. The disclosed coloration system bonds even to the smoothest of zirconia surfaces and laminating porcelain chemically bonds to the disclosed coloration system of stains.

The post-sintering coloration stains disclosed herein chemically bond to sintered zirconia after backing. The coloration system or stains may be supplied as a series of powders. The powders may be diluted using any standard dental solvent and then applied to the sintered zirconia restoration to fine tune the color and affect more natural color matching or correct any color deficiencies or inaccuracies. After the stains have been applied to the surface of the restoration, the restorations may be baked, under vacuum. The temperature may be increased by 40° C. per minute until reaching 1000° C.; may be airbaked at approximately 1000° C. for approximately 1 minute. The disclosed stains may also be used with conventional porcelains in the 850° C. to 950° C. range.

The chart below provides exemplary concentrations and sources for the various colors provided in an exemplary post-sintering coloration kit:

| # | COLOR | INGREDIENT | % | ZirChrome Suppliers List |
|---|---|---|---|---|
| 00 | CLEAR | FERRO 10 115-D | | Ferro Corp Dinnerware Systems |
| 01 | WHITE | MASON 6700 | 30.00% | 4150 East 56th Street |
| 11 | LIGHT BLUE | PEACOCK B-214 | 6.25% | Cleveland OH 44105 Phone: 216-641-8580 Fax: 216-750-7519 |
| 12 | PINK BLUE | PEACOCK B-214 | 6.25% | Mason Color Works Inc 250 East Second Street |
| | | FERRO C-1802-EZ | 2.00% | P.O. Box 76 East Liverpool, OH |
| 13 | GREY BLUE | PEACOCK B-214 | 6.25% | 43920-5076 Phone: 330-385-4400 |
| | | PEACOCK Y-3822-A | 2.50% | Fax: 330-385-4488 |
| 21 | LIGHT PINK | MASON 6001 | 25.00% | |
| 22 | DARK PINK | FERRO C-1802-EZ | 12.00% | Peacock Colors Inc 1000 National Avenue |
| 41 | YELLOW | PEACOCK Y-3849 | 15.00% | Addison, IL 60101-3175 Phone: 630-628-1960 |
| 51 | BODY ORANGE | MASON 6001 | 16.00% | Fax: 630-628-0420 |
| | | PEACOCK Y-3849 | 5.00% | |
| 52 | DEEP ORANGE | FERRO C-1802-EZ | 6.00% | |
| | | PEACOCK Y-3849 | 10.00% | |
| 53 | OCHRE | PEACOCK Y-3822-A | 8.00% | |
| | | PEACOCK B-214 | 0.30% | |
| 54 | OLIVE | PEACOCK Y-3822-A | 12.00% | |
| | | PEACOCK B-214 | 2.50% | |
| 71 | LIGHT BROWN | PEACOCK T-4679 | 12.50% | |
| 72 | DARK BROWN | PEACOCK T-4679 | 12.50% | |
| | | PEACOCK B-214 | 3.00% | |
| 73 | CHARCOAL BROWN | PEACOCK T-4679 | 12.00% | |
| | | PEACOCK B-214 | 8.00% | |
| 91 | GREY | PEACOCK B-214 | 9.00% | |
| | | PEACOCK Y-3822-A | 6.00% | |
| | | FERRO C-1802-EZ | 5.00% | |

The balance of the ingredient mixture for the above powders may be a dilutent and/or flow agent. For example, the dilutent and/or flow agent may have the following composition:

| | |
|---|---|
| Si | 53.073% |
| Ca | 23.230% |
| K | 12.840% |
| Al | 9.450% |
| Ba | 0.492% |
| Pb | 0.317% |
| Fe | 0.162% |
| Zn | 0.129% |
| Zr | 0.117% |
| Ti | 0.101% |
| Rb | 0.039% |
| Sr | 0.035% |
| Cu | 0.015% |

Method of Knife Edge Restoration with Color

Currently dental restorations require 1 mm or greater reduction in the tooth enamel. Dental reductions of this gravity may result in secondary tooth decay due to the loss of integrity of the tooth as the reduction cuts very close to the pulp, allowing infection to enter the pulp area.

Historically, 22% of restored teeth decay after 5 years. The disclosed coloring system and method allows for good color control allowing for reduced reduction of tooth enamel during the preparation for applying restoration material. Under the disclosed method, tooth reduction may be less than 1 mm, less than 0.5 mm, or even less than 0.01 mm, while maintaining good coloration and natural appearance of the restoration.

Figure 5:
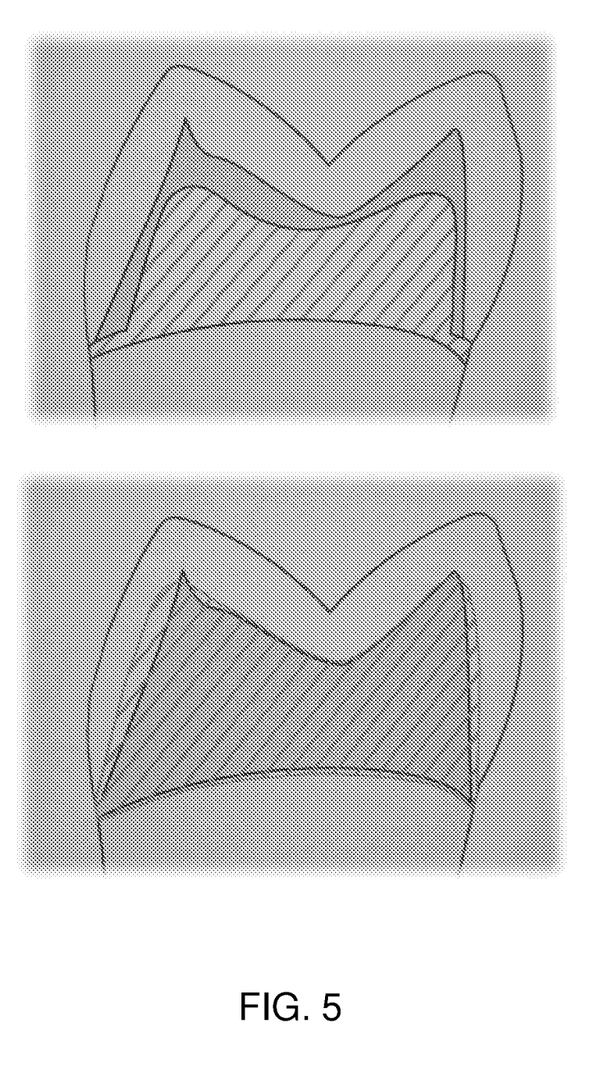
FIG. 5 illustrates the comparative protective properties of the disclosed system over the currently employed systems.

The Restoration system may be used, for example, for restoration crowns, bridges, or laminates. The method disclosed herein may include the following steps:

preparation of the tooth by reduction of about 0.001 mm-1.000 mm tooth enamel without approaching or compromising the pulp.

preparing the restoration by using the CAD/CAM or similar technologies using the presintering liquid disclosed herein to match the restoration to the natural color of the patient's existing teeth or to a color chosen by the patient or practitioner in the case of a full replacement sintering the restoration correcting the color using the post-sintering system disclosed herein covering the restoration with a glassy ceramic fitting the restoration to the patient's dentature FIG. 5 illustrates the improvement of the disclosed method and system over the currently used system. As seen, in the top drawing, traditional systems require numerous layers of material to create natural color. Therefore, the practitioner must remove enough tooth material to accommodate the multiple layers. This leaves a space between the pulp and the restoration, which may permit entry of infectious agents—leading to tooth decay. In the bottom drawing, we illustrate that under the disclosed system and method, the color system is robust enough that a very thin restoration may be used. This alleviates the need for multiple layers. In the improved method disclosed herein, the amount of tooth material a practitioner removes to accommodate the restoration is much smaller, for example about 0.001 mm-1.000 mm. As seen in the lower drawing of FIG. 5, there is no space between the restoration and the tooth and the pulp remains protected by the natural enamel. This small reduction and the maintenance of the natural enamel protects the pulp from infectious agents that cause decay.

While the foregoing written description of the invention enables one of ordinary skill to make and use what is considered presently to be the best mode thereof, those of ordinary skill will understand and appreciate the existence of variations, combinations, and equivalents of the specific exemplary embodiment and method herein. The invention should therefore not be limited by the above described embodiment and method, but by all embodiments and methods within the scope and spirit of the invention as claimed.

The invention claimed is:

1. A process for coloring Zirconia dental ceramics which comprises:

providing a pre-sintered zirconia dental ceramic restoration;

applying a coloring solution, the coloring solution comprising cobalt 2-ethyl hexanoate, iron 2-ethyl hexanoate, and chromium 2-ethyl hexanoate; and a phyto-oil;

said coloring solution capable of penetration into the zirconia dental ceramic restoration;

said coloring solution imparting a color to said dental ceramic restoration without the need to use opaque mask layers;

said coloring solution imparting a color to said dental ceramic restoration without the need to use mask layers of body porcelains.

2. The process of claim 1 wherein the phyto-oil is D-Limonene.

3. A process for coloring dental ceramics which comprises:

providing a pre-sintered Zirconia dental ceramic restoration;

applying a coloring solution, the coloring solution comprising cobalt 2-ethyl hexanoate, iron 2-ethyl hexanoate, and chromium 2-ethyl hexanoate, and mineral spirits;

said coloring solution imparting a color to said dental ceramic restoration without the need to use opaque mask layers;

said coloring solution imparting a color to said dental ceramic restoration without the need to use mask layers of body porcelains.

* * * * *